United States Patent [19] [11] 3,948,933
Fontanella [45] Apr. 6, 1976

[54] PYRROLO[1,2-c]IMIDAZOLEDIONES
[75] Inventor: Luigi Fontanella, Milan, Italy
[73] Assignee: Gruppo Lepetit S.p.A., Milan, Italy
[22] Filed: Nov. 1, 1973
[21] Appl. No.: 411,626

[30] Foreign Application Priority Data
  Nov. 3, 1972  Italy............................ 31274/72

[52] U.S. Cl.... 260/309.5; 260/247.2 R; 260/268 C;
      260/293.88; 424/248; 424/250; 424/273
[51] Int. Cl.²........................................ C07D 49/32
[58] Field of Search....... 260/309.5, 247.2, 247.2 R,
      260/268 C, 293.88

[56]        References Cited
          OTHER PUBLICATIONS
Rogers et al., J.A.C.S. – Aug. 1941, pp. 2190–2191.

Primary Examiner—Ethel G. Love
Attorney, Agent, or Firm—Theodore Post; C. Kenneth Bjork

[57]          ABSTRACT
5,6,7,7a-Tetrahydro-1H-pyrrolo[1,2-c]imidazole-1,3-(2H)-diones of the formula

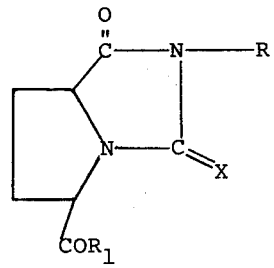

in which R is phenyl, substituted phenyl or cyclohexyl, X is oxygen or sulfur and $R_1$ is hydroxy, lower alkoxy, di-lower alkylamino-lower alkoxy, an —$NR_2R_3$ radical wherein $R_2$ and $R_3$ each independently represents hydrogen, lower alkyl, hydroxy-lower alkyl, phenyl, substituted phenyl, benzyl or together with the adjacent nitrogen atom represent a pyrrolidino, a piperidino, a morpholino or a piperazino radical. The compounds of the invention are useful as C.N.S. depressants and in particular as tranquilizing and anxiolytic agents.

7 Claims, No Drawings

PYRROLO[1,2-C]IMIDAZOLEDIONES

SUMMARY OF THE INVENTION

This invention relates to 5,6,7,7a-tetrahydro-1H-pyrrolo[1,2-c]imidazole-1,3(2H)-diones represented by formula (I)

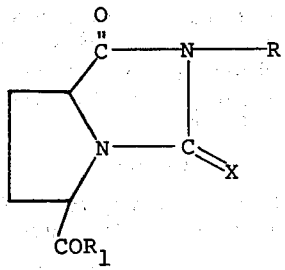

(I)

and methods of their preparation. In formula (I), R represents phenyl, substituted phenyl or cyclohexyl, X represents oxygen or sulfur and $R_1$ represents hydroxy, lower alkoxy, di-lower alkylamino-lower alkoxy, an $—NR_2R_3$ radical wherein $R_2$ and $R_3$ each independently represents hydrogen, lower alkyl, hydroxy-lower alkyl, phenyl, substituted phenyl, benzyl or together with the adjacent nitrogen atom represent a pyrrolidino, a piperidino, a morpholino or a piperazino radical.

In the specification and claims, the term "a phenyl" designates phenyl or a phenyl radical having up to two substituents selected from the group chloro, bromo, fluoro, lower alkyl, nitro, lower alkoxy, cyano, trifluoromethyl, carboxy, amino and lower acylamino; "lower alkyl" and "lower alkoxy" designate alkyl and alkoxy moieties having 1 to 4 carbon atoms; "lower acyl" designates an aliphatic acyl radical having 1 to 4 carbon atoms; "a pyrrolidine, a piperidine, a morpholine and a piperazine" designate the unsubstituted ring radicals and the respective ring radicals having substitution selected from the group lower alkyl, phenyl, benzyl and lower aliphatic acyl.

A preferred group of compounds of the invention comprises those compounds of formula (I) wherein R represents a phenyl radical, X represents oxygen and $R_1$ represents an $—NR_2R_3$ group wherein $R_2$ and $R_3$ are independently selected from hydrogen and lower alkyl.

Description of the Preferred Embodiments

The inventive compounds are prepared by cyclizing pyrrolidine dicarboxylic acid lower alkyl esters of following formula (II) according to the following scheme:

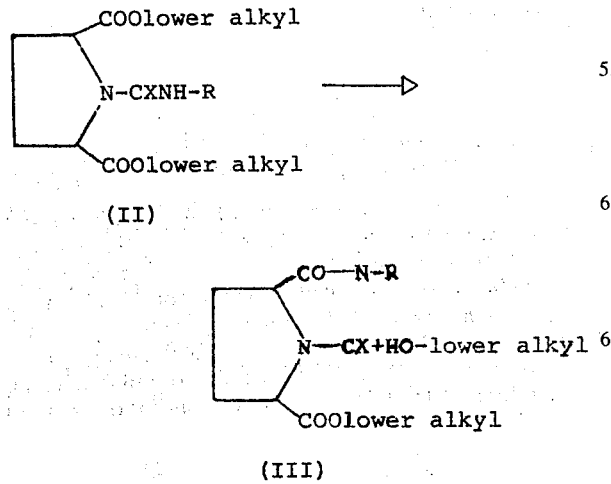

The cyclization reaction is carried out by heating the compound of formula (II) for 1 to 3 hours at a temperature from about 180° to about 260°C. The resulting esters of formula (III) are easily converted to the corresponding carboxylic acid by hydrolysis with an aqueous base or acid. In particular, aqueous alkali metal carbonates or bicarbonates, alkali metal hydroxides and strong mineral acids are advantageously employed. The compound of formula (II) may also be cyclized directly to the carboxylic acid resulting from hydrolysis of the ester of formula (III) by refluxing the former with a concentrated hydrohalide acid.

The carboxylic acids are transformed to amides or di-lower alkylamino-lower alkyl esters through conventional procedures such as, for example, by reacting an indicated amine of the formula $HNR_2R_3$ wherein $R_2$ and $R_3$ have the meaning previously given, or an indicated di-lower alkylamino-lower alkanol with the corresponding acid halide or mixed acid anhydride of the formula

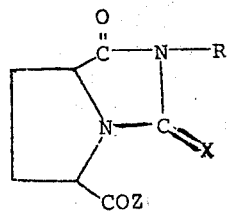

wherein R and X have the meaning previously given and Z represents chloro, bromo or the group —O—COO-lower alkyl.

The recovery of the end products from the reaction mixtures does not present particular difficulties for an art-skilled person, since usual operative methods of preparative organic chemistry are employed.

The compounds of formula (I) possess two asymmetry centes, i.e., the carbon atoms in positions 5 amd 8a, and, therefore, four isomers are theoretically possible. When a mixture of isomeric compounds is obtained, two diastereoisomers (herein referred to as α-and β-forms) may be separated by fractional crystallization, fractional distillation or chromatographic techniques. However, in some instances it is possible to obtain directly one of the two diastereoisomers since the starting materials possess a predetermined steric confirmation. Thus, from a mixture of diastereoisomeric acids of formula (I), through the reaction scheme outlined above, such as, for instance, that involving the use of mixed anhydrides, it is possible to obtain the final amide compounds in only one of the two diastereoisomeric forms. Generally this is the α-isomer since the acids of the β-form react with difficulty to give the mixed anhydrides necessary for conversion of the same acids into the corresponding amides. Each of the two diastereoisomers is in turn a racemic mixture of optical isomers (enantiomers) which are resolvable into optically active forms according to conventional procedures such as, for example, formation of salts or esters with optically active substances.

The starting materials of formula (II) for preparing the inventive compounds are obtained by addition of an isocyanate RNCX when X is oxygen or sulfur to a pyrrolidine-2,5-dicarboxylic acid lower alkyl ester. Generally, the latter is not isolated as a pure compound but is used directly for cyclization to the pyrroloimidazoledione. In those cases where it is possible to use a pure cis- or trans-pyrrolidine dicarboxylic acid lower alkyl ester, the final pyrroloimidazole compound resulting from cyclization of a pyrrolidine of formula (II) where the carbonyl groups have cis-configuration, is designated as the β-form, while that resulting from the starting compound with trans-configuration is designated as the α-form. In those other cases where a mixture of the α- and β-isomers is obtained, the separation is advantageously carried out by fractional crystallization of the carboxylic acid derived from an ester of formula (III).

Pursuant to the invention, a compound of formula (I) wherein R is a nitrophenyl group may be further transformed by reduction to the corresponding aminophenyl derivative which in turn may be acylated with a lower aliphatic acid anhydride or chloride.

The compounds of formula (I) are solid or liquid substances soluble in most common organic solvents such as, for example, 1 to 4 carbon atom alkanols, dioxane, acetone and chloroform.

The following additional description and examples further describe the invention and the manner and process of making and using it to enable the art skilled to make and use the same and set forth the best mode contemplated by the inventors of carrying out the invention.

Example 1

(a)

2-Phenyl-5,6,7,7a-tetrahydro-1,3(2H)-dioxo-1H-pyrrolo[1,2-c]imidazole-5-carboxylic acid (mixture of α- and β-isomers)

(b) α-isomer (c) β-isomer (a) 2,5-Dicarbethoxypyrrolidine (200 g.) is dissolved in 2500 ml. of diethyl ether. To this solution at 0°C., 115 ml. of phenylisocyanate in 1200 ml. of diethyl ether is added and the mixture is gradually heated to reflux temperature. Heating is continued for about 20 minutes and the solution is evaporated to dryness. The residue is the crude 2,5-dicarbethoxy-1-(phenylcarbamyl)pyrrolidine which is boiled for 45 minutes in 3400 ml. of aqueous 22% hydrochloric acid. After cooling, the resulting reaction mixture is concentrated in vacuo to half volume and the solid precipitated is recovered by filtration; yield 209 g. (86% yield). The titular mixture of isomers melts at 205°–215°C.

(b,c) The separation of the two diastereoisomers is carried out by fractional crystallization from ethanol. The less soluble fractions contain the α-isomer which melts at 232°–234°C. and the more soluble fractions contain the β-isomer which melts at 217°–220°C. After four crystallizations from ethanol, 108 g. of pure α-isomer and 60 g. of pure β-isomer are obtained. The pure α-isomer and β-isomer are obtained also by direct synthesis, pursuant to the same procedure as before, but employing as the starting materials, respectively, pure trans-2,5-dicarbethoxypyrrolidine and pure cis-2,5-dicarbethoxy-pyrrolidine (G. Cignarella et al., Gazz. Chim. Italiana 92, 1093, 1962).

Example 2

2-Cyclohexyl-5,6,7,7a-tetrahydro-1,3(2H)-dioxo-1H-pyrrolo[1,2-c]imidazole-5-carboxylic acid The compound is prepared according to the procedure described in paragraph (a) of Example 1, employing 2,5-dicarbethoxypyrrolidine and cyclohexyl isocyanate as the starting compounds. The titular compound melts at 170°–172°C.

Example 3

2-Phenyl-5,6,7,7a-tetrahydro-1,3(2H)-dioxo-1H-pyrrolo[1,2-c]imidazole-5-carboxylic acid ethyl ester 1-Phenylcarbamyl-2,5-dicarbethoxypyrrolidine (20 g.), prepared from 2,5-dicarbethoxypyrrolidine and phenyl-isocyanate, is heated under a nitrogen atmosphere at 235°–245°C. for 2 to 3 hours. The crude reaction product is purified by column chromatography through silica gel using benzene:diethyl ether 90:10 as the eluent. The titular compound boils at 202°–204°C./0.4 mm Hg.; yield 16 g.

Examples 4 – 6

Pursuant to the procedure of Example 3 and employing as the starting materials 2,5-dicarbethoxypyrrolidine and an isocyanate as indicated in the Table below, the following end compounds are obtained:

Table

| Example | Isocyanate | End Compound | M.P., °C. | B.P.,°C./mm Hg. |
|---|---|---|---|---|
| 4 | Phenyl isothiocyanate | 2-Phenyl-5,6,7,7a-tetrahydro-1-oxo-3(2H)-thiono-1H-pyrrolo[1,2-c]imidazole-5-carboxylic acid ethyl ester | 139–141 | |
| 5 | (p-Chlorophenyl)isocyanate | 2-(p-Chlorophenyl)-5,6,7,7a-tetrahydro-1,3(2H)-dioxo-1H-pyrrolo[1,2-c]imidazole-5-carboxylic acid ethyl ester | 89–91 | |
| 6 | (m-Chlorophenyl)isocyanate | 2-(m-Chlorophenyl)-5,6,7,7a-tetrahydro-1,3(2H)-dioxo-1H-pyrrolo[1,2-c]imidazole-5-carboxylic acid ethyl ester | | 198–200/0.5 |

Example 7

2-(m-Chlorophenyl)-5,6,7,7a-tetrahydro-1,3-(2H)-dioxo-1H-pyrrolo[1,2-c]imidazole-5-carboxylic acid Fifty grams of 2-(m-chlorophenyl)-5,6,7,7a-tetrahydro-1,3(2H)-dioxo-1H-pyrrolo[1,2-c]imidazole-5-carboxylic acid ethyl ester is boiled for about two hours in 500 ml. of concentrated hydrochloric acid. The reaction mixture is concentrated in vacuo to about half volume and, after cooling, the solid precipitate is recovered on a filter; yield 40 g. of the titular compound, melting at 154°–156°C. after crystallization from ethanol.

Example 8

2-(p-Chlorophenyl)-5,6,7,7a-tetrahydro-1,3(2H)-dioxo-1H-pyrrolo[1,2-c]imidazole-5-carboxylic acid Eleven grams of 2-(p-chlorophenyl)-5,6,7,7a-tetrahydro-1,3(2H)-dioxo-1H-pyrrolo[1,2-c]imidazole-5-carboxylic acid ethyl ester is boiled for 4 hours in a solution of 3.5 g. of sodium bicarbonate in 350 ml. of water. After cooling, the reaction mixture is extracted with diethyl ether and then concentrated to about 70 ml. Acidification to pH 2 with concentrated HCl gives a precipitate which is recovered by filtration, yielding 7 g. of the titular product; m.p. 246°–247°C. (ethanol).

Example 9

2-Phenyl-5,6,7,7a-tetrahydro-1-oxo-3-thioxo-1H-pyrrolo[1,2-c]imidazole-5-carboxylic acid To a solution of 1.5 g. of 2-phenyl-5,6,7,7a-tetrahydro-1-oxo-3-thioxo-1H-pyrrolo[1,2-c]imidazole-5-carboxylic acid ethyl ester in 10 ml. of methanol, 5 ml. of 1 N sodium hydroxide in 10 ml. of water is added. The mixture is allowed to stand for 3 hours at room temperaure, then methanol is evaporated in vacuo. The residual solution is extracted with diethyl ether, then acidified and concentrated to a small volume. After standing overnight, 0.7 g. of the titular product crystallizes out, m.p. 230°C. (methanol).

Example 10

(a)
α(+)-2-Phenyl-5,6,7,7a-tetrahydro-1,3(2H)-dioxo-1H-pyrrolo[1,2-c]imidazole-5-carboxylic acid (b)
α(−)-2-Phenyl-5,6,7,7a-tetrahydro-1,3-(2H)-dioxo-1H-pyrrolo[1,2-c]imidazole-5-carboxylic acid Twelve grams of α-2-phenyl-5,6,7,7a-tetrahydro-1,3-(2H)-dioxo-1H-pyrrolo[1,2-c]imidazole-5-carboxylic acid (see Example 1) and 12 g. of quinine are dissolved in 840 ml. of dry ethanol on boiling. After filtration, the solution is concentrated to about 480 ml. and is allowed to stand at room temperature for two days. The precipitate recovered by filtration is subsequently crystallized three times from dry ethanol to give a quinine salt melting at 240°–242°C. with $[\alpha]_D^{25}$—6.2(C=0.01 g./ml in benzyl alcohol). Upon acidification with dilute HCl of a concentrated aqueous solution of the quinine salts, the pure α(+)-2-phenyl-5,6,7,7a-tetrahydro-1,3-(2H)-dioxo-1H-pyrrolo[1,2-c]imidazole-5-carboxylic acid is obtained; m.p. 273°–275°C., $[\alpha]_D^{25}$ + 192(C=0.01 g./ml. in pyridine). The mother liquors of the crystallizations of the quinine salt are combined and acidified. The resulting crude precipitate (1.6 g.) is dissolved with 1 g. of ephedrine in 120 ml. of boiling acetone. The solution is concentrated to about 60 ml. and allowed to stand for two days to give an ephedrine salt which, after three further crystallizations from acetone, melts at 203°–205°C. with $[\alpha]_D^{25}$—91.4 (C=0.01 g./ml. in ethanol). Upon acidification with dilute HCl of a concentrated solution of the ephedrine salt, the pure α(−)-2-phenyl-5,6,7,7a-tetrahydro-1,3(2H)-dioxo-1H-pyrrolo[1,2-c]imidazole-5-carboxylic acid is obtained; m.p. 275°–277°C.; $[\alpha]_D^{25}$—185.7 (C=0.01 g./ml. in pyridine).

Example 11

5-Dimethylcarbamyl-2-phenyl-5,6,7,7a-tetra-hydro-1H-pyrrolo[1,2-c]imidazole-1,3(2H)-dione To a mixture of 50 ml. of diethyl ether and 50 ml. of benzene containing 3.3 g. of triethylamine in a reaction vessel, 7.8 g. of α-2-phenyl-5,6,7,7a-tetrahydro-1,3-(2H)-dioxo-1H-pyrrolo[1,2-c]imidazole-5-carboxylic acid is added and, after cooling to about 0°C., a solution of 3.3 g. of ethyl chlorocarbonate in a mixture of 30 ml. of diethyl ether and 30 ml. of benzene is added thereto dropwise. After stirring the mixture for 40 minutes, 1.5 g. of dimethylamine in 10 ml. of diethyl ether and 10 ml. of benzene are added at room temperature. Stirring is continued for one hour and the mixture is then refluxed for about 30 minutes. After cooling, the triethylamine hydrochloride by-product is precipitated by addition of about 200 ml. of diethyl ether and is filtered off. The organic solution, after washing with aqueous sodium carbonate, is dried and evaporated to dryness. The residue is dissolved in acetone, and the titular product is then precipitated by adding diethyl ether; yield 3.5 g., m.p. 172°–174°C.

Examples 12–22

Pursuant to the procedure of Example 11 employing the starting carboxylic acid and amine or alcohol derivative indicated in the following Table, the following pyrrolo[1,2-c]-imidazoldiones are obtained:

| Example | Starting materials | | End Compound | M.P.,°C. |
|---|---|---|---|---|
| | 5,6,7,7a-tetrahydro-1,3(2H)-dioxo-1H-pyrrolo[1,2-c]imidazole-5-carboxylic acid | amine or alcohol derivative | 5,6,7,7a-tetrahydro-1H-pyrrolo[1,2-c]imidazole-1,3(2H)-dione | |
| 12 | α-2-phenyl- | diethylamine | α-5-diethylcarbamyl-2-phenyl- | 120–122 |
| 13 | α-2-(m-chlorophenyl)- | diethylamine | α-5-diethylcarbamyl-2-(m-chlorophenyl)- | 108 |
| 14 | α-2-phenyl- | ethylamine | α-5-ethylcarbamyl-2-phenyl- | 122–124 |
| 15 | α-2-phenyl | dipropylamine | α-5-dipropylcarbamyl-2-phenyl- | 98 |
| 16 | α-2-phenyl- | dibutylamine | α-5-dibutylcarbamyl-2-phenyl- | 77–78 |
| 17 | α-2-phenyl | pyrrolidine | α-2-phenyl-5-pyrrolidinocarbonyl- | 178–180 |
| 18 | α-2-phenyl- | piperidine | α-2-phenyl-5-piperidinocarbonyl- | 135–137 |
| 19 | α-2-phenyl- | N-methylaniline | α-5-(N-methyl-N-phenyl)carbamyl-2-phenyl- | 122–124 |
| 20 | α-2-phenyl- | 4-methylpiperazine | α-5-(4-methyl-1-piperazinyl)carbonyl-2-phenyl- | 126–128 |
| 21 | α(+)-2-phenyl- | diethylamine | α(+)-5-diethylcarbamyl-2-phenyl- | 100–102 |
| 22 | α(−)-2-phenyl- | diethylamine | α(−)-5-diethylcarbamyl-2-phenyl- | 103–105 |

Examples 23–37

Pursuant to the procedure of Example 11 and using as the starting acids a mixture of diastereoisomeric α- and β-forms shown in the following Table, only the final amide compound of the α-form is obtained since the acid of the β-form does not react with ethyl chlorocarbonate to give the anhydride intermediate. The unreacted acid is eliminated from the final organic solution by washing with aqueous sodium carbonate.

The procedures of the previous examples are applicable in the preparation of the following compounds:

| Example | Starting Materials | | | End Compound | M.P. °C. |
|---|---|---|---|---|---|
| | -5,6,7,a-tetrahydro-1,3(2H)-dioxo-1H-pyrrolo[1,2-c]imidazole-5-carboxylic acid | M.P. °C. | amine or alcohol derivative | -5,6,7,7a-tetrahydro-1H-pyrrolo[1,2-c]imidazole-1,3(2H)-dione | |
| 23 | 2-cyclohexyl- | | diethylamine | α-2-cyclohexyl-5-diethylcarbamyl- | 102–104 |
| 24 | 2-(p-chlorophenyl)- | | p-chloroaniline | α-2-(p-chlorophenyl)-5-(p-chlorophenylcarbamyl)- | 190–200 |
| 25 | 2-phenyl- | | 2-diethylaminoethanol | α-5-(2-diethylaminoethoxy)carbonyl-2-phenyl- | 145–148 (hydrochloride) |
| 26 | 2-(m-chlorophenyl)- | | p-chloroaniline | α-2-(m-chlorophenyl)-5-(p-chlorophenylcarbamyl)- | 123–126 |
| 27 | 2-(m-chlorophenyl)- | | 3-chloro-4-methylaniline | α-2-(m-chlorophenyl)-5-(3-chloro-4-methylphenyl)carbamyl- | 105–110 |
| 28 | 2-(p-chlorophenyl)- | | p-toluidine | α-2-(p-chlorophenyl)-5-(p-tolylcarbamyl)- | 198–200 |
| 29 | 2-phenyl- | | m-chloroaniline | α-5-(m-chlorophenylcarbamyl)-2-phenyl- | 156–158 |
| 30 | 2-(p-chlorophenyl)- | | diethylamine | α-2-(p-chlorophenyl)-5-diethylcarbamyl- | 92–94 |
| 31 | 2-(p-methoxyphenyl)- | 248–250 | diethylamine | 5-(diethylcarbamyl)-2-(p-methoxyphenyl)- | 88–90 |
| 32 | 2-(o-tolyl)- | 250 | diethylamine | 5-diethylcarbamyl-2-(p-tolyl)- | 87–89 |
| 33 | 2-(o-chlorophenyl)- | 159–160 | diethylamine | 2-(o-chlorophenyl)-5-diethylcarbamyl- | 122–124 |
| 34 | 2-(o-methoxyphenyl)- | 158–161 | diethylamine | 5-diethylcarbamyl-2-(o-methoxyphenyl)- | 148–150 |
| 35 | 2-(p-tolyl)- | 250–252 | diethylamine | 5-diethylcarbamyl-2-(p-tolyl)- | 118–120 |
| 36 | 2-(m-tolyl)- | 193–195 | diethylamine | 5-diethylcarbamyl-2-(m-tolyl)- | 93–95 |
| 37 | 2-(m-trifluoromethyl)phenyl- | 169–171 | diethylamine | 5-diethylcarbamyl-2-(m-trifluoromethyl)phenyl- | 79–81 |

Example 38

β-5-Dimethylcarbamyl-2-phenyl-5,6,7,7a-tetra-hydro-1H-pyrrolo[1,2-c]imidazole-1,3(2H)-dione To a solution of 7 ml. of $SOCl_2$ in 60 ml. of dioxane, 4 g. of β-2-phenyl-5,6,7,7a-tetrahydro-1,3(2H)-dioxo-1H-pyrrolo[1,2-c]imidazole-5-carboxylic acid is added at about 5°C. After addition of 0.5 ml. of dimethylformamide, the reaction mixture is allowed to stand overnight, then is evaporated in vacuo at 20°–30°C. The crude acyl chloride obtained (4.2 g.) is dissolved in 35 ml. of dioxane, then is added at about 0°C. to a solution of 6 g. of dimethylamine in 100 ml. of anhydrous diethyl ether. After stirring for 1 hour at room temperature, the mixture is heated at reflux for 1 hour and the dimethylamine hydrochloride is filtered off.

The filtrate is evaporated to dryness and the residue is taken up with water, then extracted with chloroform.

Evaporation of the organic solution gives 4.1 g. of the titular product as a solid, which, after crystallization from methanol, melts at 162°–163°C.

Examples 39–42

Pursuant to the procedure of Example 38, the following pyrrolo[1,2-c]imidazolediones are prepared from the starting materials indicated in the Table below:

2Phenyl-5-diethylcarbamyl-1-oxo-3(2H)-thioxo-5,6,7,7a-tetrahydro-1H-pyrrolo[1,2-c]imidazole 2-Phenyl-5-phenylcarbamyl-1,3-(2H)-dioxo-5,6,7,7a-tetrahydro-1H-pyrrolo[1,2-c]imidazole 2-(m-Carboxyphenyl)-5-diethylcarbamyl-1,3(2H)-dioxo-5,6,7,7a-tetrahydro-1H-pyrrolo[1,2-c]imidazole 2-(m-Fluorophenyl)-5-diethylcarbamyl-1,3(2H)-dioxo-5,6,7,7a-tetrahydro-1H-pyrrolo[1,2-c]imidazole 2-(p-Fluorophenyl)-5-diethylcarbamyl-1,3(2H)-dioxo-5,6,7,7a-tetrahydro-1H-pyrrolo[1,2-c]imidazole 2-(m-Bromophenyl)-5-diethylcarbamyl-1,3(2H)-dioxo-5,6,7,7a-tetrahydro-1H-pyrrolo[1,2-c]imidazole 2-(m-Cyanophenyl)-5-diethylcarbamyl-1,3(2H)-dioxo-5,6,7,7a-tetrahydro-1H-pyrrolo[1,2-c]imidazole 2-(m-Nitrophenyl)-5-diethylcarbamyl-1,3(2H)-dioxo-5,6,7,7a-tetrahydro-1H-pyrrolo[1,2-c]imidazole 2-(m-Aminophenyl)-5-diethylcarbamyl-1,3(2H)-dioxo-5,6,7,7a-tetrahydro-1H-pyrrolo[1,2-c]imidazole (by catalytic hydrogenation of the previous compound)

2-(m-Acetylaminophenyl)-5-diethylcarbamyl-1,3(2H)-dioxo-5,6,7,7a-tetrahydro-1H-pyr-

| Example | Starting Materials | | End Compound | M.P.°C. or B.P.°C./mm Hg |
|---|---|---|---|---|
| | -5,6,7,7a-tetrahydro-1,3-(2H)-dioxo-1H-pyrrolo[1,2-c]imidazole-5-carboxylic acid | amine or alcohol derivatives | -5,6,7,7a-tetrahydro-1H-pyrrolo[1,2-c]imidazole-1,3(2H)-dione | |
| 39 | β-2-phenyl- | diethylamine | β-5-diethylcarbamyl-2-phenyl- | 92–94 |
| 40 | β-2-phenyl- | dipropylamine | β-5-dipropylcarbamyl-2-phenyl- | 108 |
| 41 | β-2-phenyl- | dibutylamine | β-5-dibutylcarbamyl-2-phenyl | 250/0.8 |
| 42 | β-2-phenyl- | benzylamine | β-5-benzylcarbamyl-2-phenyl | 170–172 | rolo[1,2-c]imidazole (by acetylation with acetic anhydride of the previous compound)

The depressant activity of the new pyrroloimidazolediones on the C.N.S. of animals is evidenced by testing the compounds in mice according to the Irwin method. The tranquilizing and anxiolytic activity is evaluated on the basis of the secondary conditioned response in rats. The effective dosage of representative compounds tested in animals ranges from about 10 to about 200 mg/kg i.p. The toxicity of the new compounds is very low, the $LD_{50}$ values in mice being generally higher than 500 mg/kg i.p.

In experiments in mice with the representative compound α-2-(o-chlorophenyl)-5,6,7,7a-tetrahydro-1,3(2H)-dioxo-1H-pyrrolo[1,2-c]imidazolo-5-carboxylic acid, the following $ED_{50}$ values were determined for parameters of the Irwin test which are related to sedative and hypnotic activities.

| Parameter | $ED_{50}$ |
|---|---|
| Righting reflex | 80 mg/kg i.p. |
| Impairment of motor coordination | 100 mg/kg i.p. |
| Spontaneous activity | 100 mg/kg i.p. |
| Minimal hypnotic dose | 200 mg/kg i.p. |

The $LD_{50}$ of the compound in mice is about 700 mg/kg i.p.

The representative compounds of Examples 12, 13, 14, 21, 22 and 37 when evaluated for inhibition of the secondary conditioned response which is related to anxiolytic and tranquilizng properties (Cook et al., Ann. N.Y. Acad. Sci., 66, 740, 1957; Maffii G., J. Pharm. Pharmacol., 11, 129, 1959) showed the following results in rats:

| Compound of Example | Dose mg/kg i.p. | Deconditioned/ Conditioned |
|---|---|---|
| 12 | 60 | 8/10 |
| 13 | 60 | 7/10 |
| 14 | 60 | 7/10 |
| 21 | 60 | 7/10 |
| 22 | 60 | 6/10 |
| 37 | 60 | 10/10 |

This dose level does not affect the unconditioned response and the primary conditioned response.

What is claimed is:

1. A pyrrolo[1,2-c]imidazoledione represented by the formula

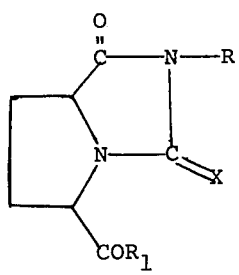

wherein R represents a phenyl or cyclohexyl radical; X represents oxygen and $R_1$ represents a hydroxy, lower alkoxy, di-lower alkylamino-lower alkoxy, or an —$NR_2R_3$ radical, wherein $R_2$ and $R_3$ each independently represents hydrogen, lower alkyl, hydroxy-lower alkyl, a phenyl or a benzyl radical, or, together with the adjacent nitrogen atom, represent a pyrrolidino, a piperidino, a morpholino or a piperazino radical.

2. A pyrrolo[1,2-c]imidazoledione represented by the formula

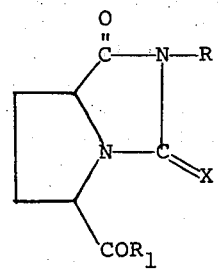

wherein R represents a phenyl radical, X represents oxygen and $R_1$ represents an —$NR_2R_3$ group wherein $R_2$ and $R_3$ are independently selected from hydrogen and lower alkyl.

3. A pyrrolo[1,2-c]imidazoledione of the formula

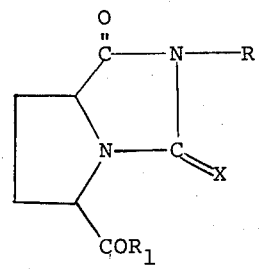

wherein R represents a phenyl radical, X represents oxygen and $R_1$ represents hydroxy.

4. A process for preparing a pyrrolo(1,2-c)imidazoledione of the formula

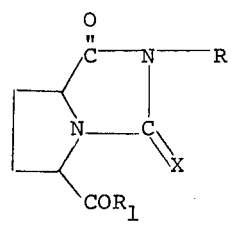

wherein R represents a phenyl or cyclohexyl radical; X represents oxygen; and $R_1$ represents hydroxy, lower alkoxy, di-lower alkylamino-lower alkoxy, an —$NR_2R_3$ radical wherein $R_2$ and $R_3$ each independently represents hydrogen, lower alkyl, hydroxy-lower alkyl, a phenyl or a benzyl radical, or, together with the adjacent nitrogen atom, represent a pyrrolidino, a piperidino, a morpholino or a piperazino radical, which comprises reacting a pyrrolidine-2,5-dicarboxylic acid lower alkyl ester with an isocyanate derivative of the formula R-CNX wherein X and R have the meaning previously given to give a compound corresponding to the formula

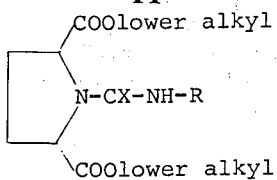

and cyclizing the latter by heating it for about 1 to about 3 hours at about 180° to about 260°C., hydrolytically cleaving the obtained lower alkyl ester with aqueous strong base or strong mineral acid, transforming the obtained carboxylic acid into the halide or mixed acid anhydride having the formula

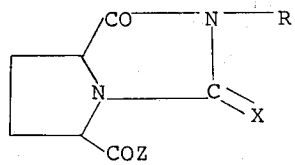

wherein Z is chloro, bromo or —O—COO-lower alkyl and reacting said compound with a diloweralkylaminolower alkanol or an amine $HNR_2R_3$, wherein $R_2$ and $R_3$ have the same meaning as above.

5. The process of claim 4 which comprises heating a compound of the formula

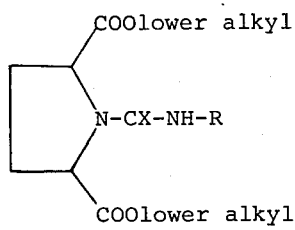

at reflux temperature, whereby the compound is cyclized.

6. The process of claim 4, which comprises cyclizing a compound of the formula

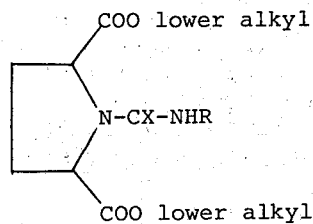

by heating it to reflux temperature in concentrated hydrochloric acid.

7. A compound represented by the formula

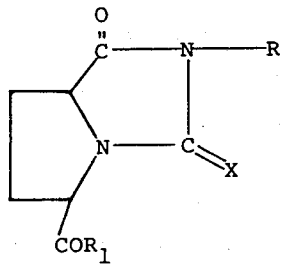

wherein $R_1$ represents an $—NR_2R_3$ radical, wherein $R_2$ and $R_3$ each independently represents hydrogen, lower alkyl, hydroxy-lower alkyl, a phenyl or a benzyl radical, or, together with the adjacent nitrogen atom, represent a pyrrolidino, a piperidino, a morpholino or a piperazino radical.

* * * * *

UNITED STATES PATENT AND TRADEMARK OFFICE
CERTIFICATE OF CORRECTION

PATENT NO. : 3,948,933
DATED : April 6, 1976
INVENTOR(S) : Luigi Fontanella

It is certified that error appears in the above-identified patent and that said Letters Patent are hereby corrected as shown below:

Column 2, line 46, "centes," should read --centers,--;

Column 2, line 46, "5 amd 8α," should read --5 and 7α,--;

Column 5, line 24, "temperaure," should read --temperature,--;

Column 8, in Table under last column, "(hydrochloride" should read --(hydrochloride)--;

Column 8, line 31, "2Phenyl" should read --2-Phenyl--;

Column 9, line 32, "tranquilizng" should read --tranquilizing--.

Signed and Sealed this

Seventeenth Day of August 1976

[SEAL]

Attest:

RUTH C. MASON
Attesting Officer

C. MARSHALL DANN
Commissioner of Patents and Trademarks